United States Patent
Kraus et al.

(10) Patent No.: US 6,750,032 B2
(45) Date of Patent: Jun. 15, 2004

(54) METHOD AND DIAGNOSTIC AGENT FOR HEMOSTASIS DIAGNOSIS

(75) Inventors: Michael Kraus, Marburg (DE); Carsten Schelp, Marburg (DE); Andreas Wiegand, Schwalmstadt (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 10/255,632

(22) Filed: Sep. 27, 2002

(65) Prior Publication Data

US 2003/0027235 A1 Feb. 6, 2003

Related U.S. Application Data

(62) Division of application No. 09/604,271, filed on Jun. 26, 2000, now Pat. No. 6,482,653, which is a continuation of application No. 09/215,167, filed on Dec. 18, 1998, now Pat. No. 6,187,594.

(30) Foreign Application Priority Data

Dec. 19, 1997 (DE) .......... 197 56 773

(51) Int. Cl.$^7$ .......... C12Q 1/52; G01N 33/86; G01N 33/546
(52) U.S. Cl. .......... 435/16; 436/69; 436/533
(58) Field of Search .......... 435/16; 436/69, 436/533

(56) References Cited

U.S. PATENT DOCUMENTS

| | | | | |
|---|---|---|---|---|
| 3,700,408 | A | 10/1972 | Bicher | 23/230 B |
| 3,996,345 | A | 12/1976 | Ullman et al. | 435/12 |
| 4,051,236 | A | 9/1977 | Harris | 424/101 |
| 4,110,161 | A | 8/1978 | Sekkar | 195/1.8 |
| 4,429,040 | A | 1/1984 | Becker et al. | |
| 4,663,278 | A | 5/1987 | DiNello | 435/7 |
| 4,668,621 | A | 5/1987 | Doellgast | 435/13 |
| 5,118,182 | A | 6/1992 | Carr, Jr. | 356/39 |
| 5,340,716 | A | * 8/1994 | Ullman et al. | 435/6 |
| 5,527,684 | A | 6/1996 | Mabile et al. | 435/7.1 |
| 5,563,041 | A | 10/1996 | Reers | 435/13 |
| 5,567,596 | A | 10/1996 | Diamond | 435/4 |
| 6,187,594 | B1 | 2/2001 | Kraus et al. | |

FOREIGN PATENT DOCUMENTS

| | | | |
|---|---|---|---|
| EP | 0 515 194 A2 | 11/1992 | |
| WO | WO 95/06877 | 3/1985 | |
| WO | WO 97/28261 | 8/1997 | |

OTHER PUBLICATIONS

C. Masson et al., "Kinetic analysis of the Interaction between plasminogen activator inhibitor–1 and tissue–type plasminogen activator," Biochem. J., 256:237–244 (1988).
S. Bystryak et al., "A Homogeneous Immunofluorescence Assay Based on Dye–Sensitized photobleaching," Analytical Biochemistry, 255:127–134 (1995).
H. Hart et al., "Scintillation Proximity Assay (SPA)—A New Method of Immunoassay," Molecular Immunology, 16:265–267 (1979).
G. Mathis, "Rare Earth Cryptates and Homogeneous Fluoroimmunoassays with Human Sera," Clin. Chem., 39(9):1953–1959 (1993).
E. Ullman et al., "Luminescent oxygen channeling assay (LOCI™); sensitive, broadly applicable homogeneous immunoassay method," Clin. Chem., 42(9):1518–1526 (1996).
R. Colman et al., "Plasma Coagulation Factors," Hemostasis and Thombosis, 3:3–18 (1994).
R. Colman et al., "The Plasinogen–Plasmin Enzyme System," Hemostasis and Thrombosis, 3:1592–1622 (1994).
S. Udenfriend et al., "Scintillation proximity radioimmunoassay utilizing $^{125}$I–Labeled ligands".
E. Ullman et al., "Luminescent oxygen channeling immunoassay: Measurement of particle of particle binding kinetics by chemiluminescene," Proc. Natl. Acad. Sci., 91:5426–5430 (1994).
European Search Report dated Jan. 18, 2002.
M. Steiner, "Changes in the Distribution of Platelet Membrane Proteins Revealed by Energy Transfer," Biochimica et Biophysica Acta., 805(1):53–58 (1984).

* cited by examiner

*Primary Examiner*—Jon P. Weber
(74) *Attorney, Agent, or Firm*—Finnegan, Henderson, Farabow, Garrett and Dunner, L.L.P.

(57) ABSTRACT

The invention relates to a method and to a diagnostic agent for detecting hemostasis disturbances, wherein, as a consequence of blood platelet aggregation, clot formation and/or clot dissolution, substances are brought to a distance from each other which permits or prevents an interaction, in particular an energy transfer, between the substances, and the extent of the interaction is measured.

13 Claims, 3 Drawing Sheets

METHOD AND DIAGNOSTIC AGENT FOR HEMOSTASIS DIAGNOSIS

This is a division of application Ser. No. 09/604,271, filed Jun. 26, 2000, which issued as U.S. Pat. No. 6,482,653, on Nov. 19, 2002, which is a continuation of application Ser. No. 09/215,167, filed Dec. 18, 1998, which issued as U.S. Pat. No. 6,187,594, on Feb. 13, 2001, all of which are incorporated herein by reference.

The invention relates to a method and to a diagnostic agent for detecting hemostasis disturbances, wherein, as a consequence of blood platelet aggregation, clot formation and/or clot dissolution, substances are brought to a distance from each other which permits or prevents an interaction, in particular an energy transfer, between the substances, and the extent of the interaction is measured.

The bloodstream supplies the organs with nutrients, and provides for the disposal of metabolic products, by way of the vascular system. The maintenance of an open vascular system, which is nevertheless sealed off against the environment, is therefore of vital importance. This is made possible by the interaction of the opposing systems of blood coagulation and fibrinolysis—which are in an equilibrium, termed hemostasis, with respect to each other. In extreme cases, a disturbance of these systems is manifested clinically either in thromboses, i.e. unintentional occlusions of the vascular system, or in a hemorrhagic diathesis, i.e. bleeding. Both phenomena can lead to death by way of organ failure. They represent one of the main causes of mortality in the western world. An important role is therefore attached in clinical diagnosis to detecting an acquired or inherited hemostasis disturbance.

The processes of hemostasis are based on the interaction of blood vessels (contraction and dilatation), cells (the endothelium lining the blood vessels and/or thrombocytes which are floating in the blood vessels) and humoral factors. A distinction is made between primary and secondary coagulation in accordance with the physiological sequence of the processes. The cellular components dominate in primary coagulation and this coagulation concludes with the formation of thrombocyte aggregates (primary clot). The humoral factors dominate in secondary coagulation, which is normally initiated by the cellular components. These humoral factors are proteins, which are essentially differentiated, in accordance with their function, into enzymes, cofactors and supporting proteins. When coagulation is activated, active or activated enzymes proteolytically convert proenzymes, by way of a cascade-like system, into their active form. This activity can be increased by means of cofactors which are for the most part themselves proteolytically activated. As the last step, the supporting protein fibrinogen, which is soluble in its precursor form, is converted by the coagulation enzyme thrombin into its insoluble resultant product, i.e. fibrin. The fibrin clot (secondary clot) is produced by the aggregation and enzymic crosslinking of the fibrin. Primary and secondary coagulation promote wound healing. Under pathological circumstances, however, the bloodstream becomes unintentionally blocked, an event which is clinically described as thrombosis. The clots are dissolved by the fibrinolysis system, which leads, by way of a similar succession of activating enzymes, to activation of the protease plasmin. Under the pathological circumstances of hyperfibrinolysis, plasmin nonspecifically destroys fibrinogen which has still not clotted and thereby disrupts the integrity of the capillary system, resulting in bleedings.

Diagnostic methods, which are differentiated into so-called
- classical methods,
- clinical chemistry methods, and
- immunochemical methods, are used to investigate the above-described processes for the purpose of detecting possible disturbances of hemostasis.

The diagnostic methods which are termed classical methods are based on detecting the formation of a clot. Those methods predominate which activate the activation cascades of coagulation and/or of fibrinolysis at one point and measure the time until a clot has formed or dissolved. Changes in these coagulation or fibrinolysis times as compared with a normal sample enable conclusions to be drawn with regard to pathological changes which have taken place in the constituent section which has been activated, i.e. the section of the reaction cascades up to the formation or dissolution of a fibrin aggregate. In the classical methods, the clot is normally detected by means of mechanical or optical detection methods.

Mechanical detection uses the increased viscosity of the coagulating sample or the formation of fibrin threads. For example, a sphere or a stirring flea is placed in the bottom of a reaction vessel and coagulation is induced in the blood sample which is added to the vessel. The sphere or the stirring flea or the vessel rotate and the force required for this movement is measured. If the viscosity of the solution increases due to platelet aggregation or clot formation, this is measured as an increased resistance and, from a particular value onwards, assessed as being the onset of coagulation. In another method (in accordance with Schnitger & Gross), a hook-shaped electrode is dipped into the sample and withdrawn from it at regular intervals. In association with this, the supply of current to an electrode which is lying in the sample is switched on and off in a corresponding manner. If a fibrin thread is formed, the mobile electrode becomes entangled and the flow of current is maintained. This is interpreted as the onset of coagulation. Conversely, when fibrinolysis is being diagnosed, the dissolution of the clot is detected in a corresponding manner by a decrease in the viscosity or the dissolution of the fibrin.

In the classical methods, mechanical detection has the advantage that it registers the physiologically important property of clot formation, namely the mechanically stable closure of a wound. On the other hand, this technique requires special equipment which is only suitable for these special hemostasis tests.

Optical detection is understood to mean turbidimetric determination of the change in the turbidity of the solution when a clot is formed. The turbidity signal associated with a fibrin clot can be amplified by means of methods which are known to the skilled person, for example by means of increasing the optical density of the sample, for example by adding particles, or by means of augmenting the denaturation of the fibrin by adding salts or ions, for example metal ions such as manganese, iron or calcium ions. In the classical methods, optical detection is not understood to mean the conversion of chromogenic substrates, which can likewise be measured photooptically, since this records an enzyme activity and not the aggregation of thrombocytes or conversion of the natural supporting protein fibrinogen.

EP 0 039 885 reports that hydrophobic latex particles can be used for detecting fibrin monomers, i.e. fibrin which has still not polymerized. However, such simple latex particles are not suitable for detecting a clot since the agglutination of latex particles causes increased light scattering which cannot be distinguished from the light scattering which a fibrin clot itself produces.

An advantage of optical detection is the possibility of carrying out the measurements on current clinical chemistry automated analytical equipment. However, since optical detection is based on measuring turbidity, turbidities in samples, e.g. in the case of hyperlipemic samples, can, in contrast to mechanical detection, interfere with the determination. In extreme cases, for example in the case of whole blood, no optical detection is possible at all, due to the optical density. This is an important disadvantage of these optical methods.

In addition to the above-described conventional classical diagnostic methods, the clinical chemistry methods are also customarily used in hemostasis diagnosis. These methods use the conversion of specific, chromogenic substrates, on their own or in combination with enzymes and/or intermediates (enzymatically coupled test) to measure the activity of individual enzymes. These determinations are independent of the formation of a thrombocyte aggregate or of a fibrin clot. A disadvantage in this context is, however, that the physiologically relevant reactions, namely disturbances in the formation of a thrombocyte aggregate or a fibrin clot, or their dissolution, e.g. a dysfibrinogenemia or a restricted reactivity of the coagulation enzymes with phospholipid surfaces due to a vitamin K deficiency or therapy with coumarin, are not recorded.

The immunochemical methods are rather uncommon in hemostasis diagnosis since, in this case, it is the diagnosis of functional disturbances, and to a lesser extent the determination of the quantity of an analyte to be detected, which is of importance. Nevertheless, the immunochemical detection of cleavage products from the proteolytic action of the cascade reactions, or the detection of protease/inhibitor complexes, enables conclusions to be drawn with regard to the current activity of the relevant systems. These conclusions can be useful in differential diagnosis. At present, the use of immunochemical methods in hemostasis diagnosis is mainly restricted to research studies.

The invention was based on the object of finding a novel detection method which enables the classical mechanical methods to be carried out on current automated analytical equipment as well and which proves to be robust in relation to the interference, which is customary in optical methods, arising from sample turbidities, such that it becomes possible to carry out a measurement in whole blood as well.

According to the invention, this object is achieved by a method or by a diagnostic agent as claimed in the claims, in particular by a method for detecting a hemostasis disturbance, wherein, as a consequence of blood platelet aggregation, clot formation, and/or clot dissolution, substances are brought to a distance from each other which permits or prevents an interaction, in particular an energy transfer, between the substances, and the extent of interaction is measured.

The term hemostasis disturbance means all inherited or acquired disturbances of the coagulation system, the fibrinolysis system and the complement system, in particular deficiencies or deficits of the factors and regulators which are involved in these systems, and also of receptors for these factors and regulators, insofar as these receptors come to be used in the test assay as a result of the presence of tissue, tissue parts and/or cells.

Conclusions with regard to the processes of blood platelet aggregation, clot formation and/or clot dissolution can be drawn by determining the extent to which the substances interact—e.g. by directly or indirectly measuring the quantity of energy transferred. When this method is used, therefore, the advantages of the classical mechanical methods (direct measurement of the physiological process of clot formation or dissolution) and the classical, optical hemostasis-diagnosis methods (measurement on customary automated analytical equipment) can be combined without their disadvantages (e.g. sensitivity to interference with regard to turbid samples) being assumed at the same time. Thus, the novel method can accordingly be used to measure all the samples, such as blood platelet-poor plasma, blood platelet-rich plasma or whole blood, which are customary in hemostasis diagnosis.

Whole blood represents the maximum of interference for optical methods. Because of the erythrocytes which are present, the optical density is so high that it is not possible to carry out a measurement on currently available equipment which measures optically. The course of the coagulation reaction in whole blood samples, as determined by the novel method, is practically unaffected. This makes it possible to use the novel method for determining whole blood samples at point of care or in home diagnosis. Since primary and secondary coagulation interact in the coagulation of whole blood, the entire process can be determined using the novel method. The novel method can consequently be used both for determining the humoral factors and for determining the coagulation or lysis activity of cellular components.

The novel method makes it possible to carry out the entire hemostasis diagnosis on one single piece of equipment, since the corresponding clinical chemistry and immunochemical hemostasis-diagnosis methods can also be adapted with the novel method in mind: for example, instead of the customary chromogenic substrates, use can be made of substances which are capable of effective energy transfer and which are, for example, linked by way of an appropriate, enzymically cleavable peptide chain (see, for example, WO 97/28261). In this context, one or more of the substances can be linked, directly or indirectly, e.g. by way of linkage systems, such as antigen/antibody or avidin/biotin, to the peptide chain so that the enzymic reaction can take place before or after the linkage of the substance(s) to the peptide chain, or else at the same time as this linkage.

Within the context of the overall invention, the term "substances" is to be understood as meaning members of biological and/or chemical substance classes which, when in spatial proximity, can enter into interaction with each other, e.g. in the form of energy donors and energy recipients, such as, for example, photosensitizers and chemiluminescers (EP 0 515 194; Ullman et al. (1996) Clinical Chemistry 42:1518–1526), photosensitizers and fluorophores (WO 95/06877; Bystrak et al. (1995) Anal. Biochem. 225:127–134), or radioactive iodine$^{125}$ and fluorophores (S. Udenfriend et al. (1985) Proc. Natl. Acad. Sci. 82:8672–8676), or fluorophores and fluorophores (Mathis, G. (1993) Clin. Chem. 39:1953–1959) or fluorophores and fluorescence quenchers (U.S. Pat. No. 3,996,345).

An interaction between the substances is to be understood, in particular, as meaning an energy transfer—that is the direct transfer of energy between the substances, e.g. by means of light or electron radiation as well as by way of reactive chemical molecules. While the energy transfer can take place from one substance to another substance, it is also possible for the energy transfer to run through a cascade of different substances.

In addition, the phrase "interaction between the substances" also encompasses processes in which the activity of a substance is inhibited or augmented by one or more different substances, for example inhibition of or increase in the enzyme activity, or the inhibition of, the increase in or change of (e.g. wavelength displacement, polarization) the light which is emitted by the affected substance.

The phrase "interaction between the substances" is furthermore also to be understood as meaning enzyme cascades (cf. U.S. Pat. No. 4,663,278). In this case, the substances are enzymes, at least one of which supplies the substrate for another enzyme, wherein, as a consequence of blood platelet aggregation, clot formation and/or clot dissolution, the enzymes are brought to a distance from each other such that the reaction velocity of the coupled substrate conversion achieves a maximum or a minimum. In this way, the following variants can, for example, be effected:

(a) Enzyme E1 (=substance A) produces the substrate "a" for the enzyme E2 (=substance B), which substrate is converted by enzyme E2 into a measurable end product or intermediate "b". If the enzymes are in solution, the diffusion path for the substrate "a" to reach enzyme E2 is relatively long, and the kinetics of the conversion into "b" is consequently slow. If the enzymes E1 and E2 are spatially adjacent, for example as the consequence of clot formation or blood platelet aggregation, this then results in the kinetics of the conversion to "b" being more rapid.

(b) The enzymes E1 (=substance A) and E3 (=substance C) are in spatial proximity from the start; they are, for example, both bound to the same particles. The enzyme E1 forms the substrate for the enzyme E2 (substance B), with enzyme E2 producing the substrate for enzyme E3. The method proceeds in analogy with (a), with all three substances being brought into spatial proximity as the result of clot formation or blood platelet aggregation, or with an arrangement involving spatial proximity being abolished as the result of clot dissolution.

An effective interaction between the substances takes place when these substances are spatially adjacent, that is, for example, within a distance range of a few $\mu$m, in particular within a distance range of less than 600 nm, preferably less than 400 nm, and very particularly preferably less than 200 nm.

In a preferred embodiment of the novel method, the interaction between the substances is effected as an energy transfer, for example by means of short-lived molecules, e.g. singlet oxygen (see also EP 0 515 194; Ullman et al. (1994) Proc. Natl. Acad. Sci. 91:5426–5430; Ullman et al. (1996) Clinical Chemistry 42:1518–1526, WO 95/06877 and Bystrak et al. (1995) Anal. Biochem. 225:127–134), short-range radiation, e.g. radioactive β radiation (see Hart & Greenwald (1979) Molecular Immunology 16:265–267 and Udenfriend et al. (1985) Proc. Natl. Acad. Sci. 82:8672–8676), and/or energy transfer in accordance with Förster (Mathis, G. (1993) Clin. Chem. 39:1953–1959; U.S. Pat. No. 5,527,684).

In another preferred embodiment of the novel method, the activity of substances is augmented or inhibited by other substances and this leads to a measurable change in signal, for example change in the intensity or polarization of the emitted light, inhibition of or increase in enzyme activities and/or change in fluorescence behavior.

The novel method also encompasses embodiments in which at least one of the substances is able to bind nonspecifically, e.g. by means of hydrophobic or electrostatic interaction, to components of a blood clot which is forming or which is dissolving. This binding may take place directly by way of an interaction between the substance and the components of the blood clot which is forming or dissolving or indirectly, by means of the substance being bound to blood clots which are forming or dissolving by way of binding-mediating components such as polymers which are linked to the substance and which occur naturally or are prepared synthetically, proteins, in particular fragments of fibrinogen, sugars, lipids or peptides, in particular those peptides which possess the amino acid sequence RGD, or, particularly preferably, particles.

Particularly advantageous embodiments of the novel method are distinguished by the fact that one or more substances are bound covalently, by way of a specific interaction and/or adsorptively to suspendable particles, and/or are incorporated into these particles or themselves constitute suspendable particles or a part thereof. The term suspendable particles is to be understood as meaning particles such as dye crystals, metal sols, silica particles, magnetic particles, oil drops, lipid particles, dextran, protein aggregates or, particularly preferably, latex particles. Preference is given to particles having a diameter of 0.01–10 $\mu$m, particularly preferably having a diameter of 0.05–3 $\mu$m, very particularly preferably having a diameter of 0.05–1 $\mu$m.

In the case of a covalent bond, the substances are linked by way of a chemical bond to the particles or to any possible shells or layers which coat the particles. Substances can also be linked to the particles or particle coatings by way of specific interactions, e.g. mediated by way of antibodies, lectins, receptors, biotin/avidin or complementary nucleotide strands. As a rule, adsorptive binding is due to hydrophobic, hydrophilic or electrostatic interactions between the particles or particle coatings and the substances. Incorporation of the substances into one or more particle cavities, which can also be formed by particle coatings, is also effective.

The novel method also encompasses embodiments in which the surface of the particles is modified further after the particles have been prepared and/or the particles are coated by one or more covalently or adsorptively bound layers or shells, e.g. composed of proteins, carbohydrates, lipophilic substances, biopolymers, organic polymers, or mixtures thereof, in order to achieve, for example, improvements with regard to suspension stability, storage stability, formative stability or resistance to UV light, microbes or other agents having a destructive effect. The modifications and coatings can likewise serve the purpose of reducing or preventing nonspecific binding to surfaces of reaction vessels and to those of sample constituents, such as, in particular, proteins (e.g. albumin or antibodies) or cell constituents (e.g. phospholipids or nucleic acids). The modifications and coatings can furthermore serve the purpose of increasing or decreasing the hydrophobicity of the particle surface or the charge on the surface of the particles.

By means of making such changes in the particle surface, it is possible to improve the binding of the particles to blood clot components and make this binding more selective. The ability of the substances to bind specifically to components of a blood clot which is in the process of forming or dissolving is an important prerequisite for the functioning of the novel method. Whether the substances to be employed possess this property per se, or whether binding-mediating components are required, can be established by means of binding tests, as explained below using the example of particle-bound substances:

Particles which are suitable for use as binding-mediating components can be selected by examining the binding of the particles to an immobilized fibrin surface. Such a fibrin surface can be prepared, for example, by the method of Masson & Angles-Cano (Biochem. J. (1988) 256: 237–244), which is briefly as follows: polyvinyl chloride receptacles are preactivated, at room temperature for 2 hours, with a 2.5% (v/v) solution of glutaraldehyde in 0.1 M sodium bicarbonate buffer (pH 9.5), and a fibrinogen-containing solution (0.3 μmol/l in 0.1 M sodium phosphate buffer (pH 7.4), containing 1 mmol of calcium chloride/l) is then applied. When commercially available small polystyrene tubes or microtitration plates which have, for example, been preactivated by gamma irradiation are used for the protein coating, the test receptacles employed can be brought directly into contact with a fibrinogen-containing solution. After an incubation of several hours, usually overnight (approx. 18 hours), unbound fibrinogen is removed by washing with a detergent-containing washing buffer (e.g. from the Dade Behring Marburg GmbH Enzygnost line). The bound fibrinogen is converted into fibrin by adding thrombin (1 NIH unit/ml in 50 mM tris-HCl; 1 mM $CaCl_2$; pH 7.4; for example Test Thrombin Reagent; Dade Behring Marburg GmbH), and the thrombin is then removed by washing, e.g. using a solution containing 0.5 M NaCl; 8 mM $CaCl_2$ and 0.05% Tween 20. After a further washing step using a customary detergent-containing washing buffer, free binding sites on the fibrin solid phase are saturated by washing once with a 0.2% (w/v) solution of bovine serum albumin. The binding of the particles to be investigated, e.g. latex particles containing photosensitizers (sensitizer particles) in combination with latex particles containing chemiluminescent compounds (chemiluminescer particles) (see also Clin. Chem. (1996) 42:1518–1526), to the fibrin surface is tested by adding the particles to the coated test receptacles in a neutral buffer (for example: 50 mM tris-HCl; 0.9% NaCl; 0.05% Tween 20; pH 7.4). After an incubation of 10 min (shorter or longer incubation times are also to be recommended depending on the material under investigation), the fibrin-coated test receptacle is washed once or more with the same buffer and the energy transfer between the sensitizer particles and chemiluminescer particles, which are adhering to the washed test tube, is measured in a suitable measuring device, for example as described in more detail in example 1. In order to exclude particles which possess the undesirable property of also binding to fibrinogen, the particles can be incubated in the presence of increasing concentrations of fibrinogen. The binding of fibrinogen-binding particles to the fibrin-coated surface is markedly reduced by the fibrinogen, which is added up to a concentration of 5 g/l, and the measured signal is thereby ultimately decreased. Other binding-mediating components which are suitable for the novel method can also be found in analogy with this method.

A particularly preferred embodiment of the novel method is that in which photosensitizers, for example acetone, benzophenone, 9-thioxanthone, eosin, 9,10-dibromo-anthracene, chlorophyll, buckminsterfullerene, methylene blue, Rose Bengal, porphyrins, phthalocyanines and/or their derivatives, and chemiluminescent compounds, for example olefins, 9-alkylidenexanthans, 9-alkylidene-N-alkylacridans, enol ethers, enamines, arylvinyl ethers, dioxenes, arylimidazoles and/or lucigenin, are employed as substances, and the singlet oxygen which is generated by the photosensitizer is able to activate the chemiluminescent compounds thereby causing them to emit light. In the novel method, preference is also given to using substances, such as luminol and oxalate esters, which react with singlet oxygen to form intermediates which are able to react, with the emission of light, with reagents which are known to the skilled person.

As a rule, the chemiluminescent compounds emit light in wavelength ranges above 300 nm. The fluorescence of plasma falls rapidly in the 500 nm range and can be disregarded above 550 nm. If higher wavelengths are required, the chemiluminescent compounds can, according to the invention, also be brought into contact with fluorophores which are able to be stimulated by the activated chemiluminescent compounds and emit at higher wavelengths. Examples of suitable fluorophores are rhodamines, ethidium bromide, 5-dimethylamino-1-naphthalenesulfonyl, europium chelates with the agent 3-(2-thienoyl)-1,1,1-trifluoroacetone [$Eu(TTA)_3$ (TTA=3-(2-thienoyl)-1,1,1-trifluoroacetone)] or ruthenium chelates with the agent 2,2'-dipyridyl [$Ru(bpy)_3^{++}$ (bpy=2,2'-dipyridyl)].

Another preferred embodiment of the novel method is that in which photosensitizers and fluorescent compounds are employed as substances and the singlet oxygen which is generated by the photosensitizer is able to activate the fluorescent compound, thereby causing it to emit light, or to suppress the emission of light in a quenching process. Preference is given, in particular, to novel methods in which fluorescent compounds are used which, as the result of reaction with singlet oxygen, are subject to a photo-oxidation, i.e. a "photobleaching", for example, 1,3-diphenylisobenzofuran, or which react with singlet oxygen, as photoactive precursors, to give fluorophores, for example oxene umbelliferyl ethers or umbelliferyl selenides.

For further examples of particles, photosensitizers and chemiluminescent or fluorescent compounds which are suitable for the novel method, the reader is referred, in particular, to EP 0 515 194, Ullman et al. (Proc. Natl. Acad, Sci. 91:5426–5430, 1994) and Ullman et al. (Clinical Chemistry 42:1518–1526, 1996, WO 95/06877).

The novel method can, for example, be used for detecting:

a genetically determined and/or acquired deficiency of factors of the blood coagulation system, such as von Willebrand factor, factors (factor=F) of the extrinsic system, such as FVII, FX, FII, FV or protein Z, factors of the intrinsic system, such as FXII, prekallikrein, high molecular weight kininogen, FXI, FIX or FVIII, or control system factors, such as antithrombin III, tissue factor pathway inhibitor, protein C or protein S or C1 inhibitor, a genetically determined and/or acquired deficiency of factors of the fibrinolysis system, such as tissue plasminogen activator, urinary plasminogen activator, plasminogen, α2-antiplasmin, plasminogen activator inhibitors 1, 2 and 3 or thrombin-activatable fibrinolysis inhibitor (TAFI), genetic defects of thrombocytes, such as Bernard Soulier syndrome, Glanzmann's thrombasthenia, dense body deficiency, α-granule deficiency or thromboxane synthesis defects, acquired hemostasis disturbances, e.g. resulting from diseases or disease states such as uremia, myeloproliferative disorders, solid tumors, storage pool disease or inflammations, in particular those inflammations which give rise to proteolytically or oxidatively modified proteins, for example of the protein C system, anti-thrombin III and/or plasminogen activator inhibitor 1, acquired hemostasis disturbances resulting from the administration of therapeutic agents which exert an effect on the activity of one or more components of the hemostasis system, e.g. heparin, coumarin derivatives, hirudin, contact phase inhibitors, such as bovine trypsin inhibitor or C1 esterase inhibitor, aspirin or antibodies against platelet receptors, or genetic and/or acquired defects of the complement system.

The novel method can also be used to determine the time required for forming a fibrin clot. In one embodiment of the novel method, clot formation is induced, in a plasma or in a medium which at least contains fibrinogen and/or blood platelets, by adding substances which induce coagulation, such as enzymes, e.g. those derived from snake venoms, or thrombin, or other active proteases, or by surface-active substances, such as silicates or phenol derivatives, or by activated blood platelets or blood platelet-activating substances, such as thrombin, collagen, adrenalin or adenosin diphosphate, or by the optional addition of coagulation-supporting substances, such as buffering substances, calcium chloride and/or phospholipids, or one or more of these substances.

The novel method can be used to determine the activated partial thromboplastin time (APTT), the thromboplastin time (PT), the protein C activation time (PCAT), the Russell's viper venom time (RVVT) or the thrombin time.

The activated partial thromboplastin time (APTT) registers disturbances of the intrinsic pathway of the humoral coagulation system. The thromboplastin time registers disturbances in the extrinsic pathway of the humoral coagulation system (see also Colman R W et al. Overview on Hemostasis. In: Colman R W, Hirsh J, Marder V J, Salzman E W, eds., Hemostasis and Thrombosis, J.B. Lippincott Company, 3rd Edition, 1994; pages 3–18). Tests for determining these disturbances are screening tests which in each case require all the components of the relevant branch of the humoral coagulation system up to the formation of thrombin, which converts fibrinogen into the fibrin clot.

In order to determine the factors of the fibrinolysis system, the sample to be measured is, in a preferred embodiment of the novel method, substituted with the factors which are required for clot formation, for example by means of mixing with a deficient plasma or by adding purified factors such as urinary plasminogen activator (uPA), tissue plasminogen activator (tPA), $\alpha_2$-antiplasmin, plasminogen, plasminogen activator inhibitor 1 and/or factor XII, in particular fibrinogen. In particular embodiments of the novel method, a spontaneous lysis can be induced or a lysis can be induced after adding activators, such as factor XIIa, tPA, uPA or streptokinase, or directly after adding plasmin.

In a particularly preferred embodiment of the invention, the time at which the lysis of a fibrin clot begins is determined by means of a signal increase: A plasma is caused to coagulate. The clot is lysed by adding, for example, streptokinase, which is an enzyme from Streptococcus which activates plasmin. In conventional methods, this lysis is seen as a continuous decrease in the measured signal. However, the beginning of the dissolution of the clot is difficult to establish since the decrease in signal takes place gradually when optically measuring instruments are used. Surprisingly, in the novel method, the signal increases abruptly and very markedly when the lysis begins. This is not due to the added streptokinase interfering with the test components, since the streptokinase is present from the start of the measuring period onwards.

This surprising effect which has been found offers the novel possibility of determining the beginning of a lysis very precisely. This extends the possibilities for diagnosing the fibrinolytic system, for example for determining individual factors as well as the entire system or for determining fibrinolysis which is mediated by factor XIIa, uPA or tPA (Bachmann F. The plasminogen-Plasmin Enzyme System. In: Colman R W, Hirsh J, Marder V J, Salzman E W, eds., Hemostasis and Thrombosis, J.B. Lippincott Company, 3rd Edition, 1994; pages 1592–1622). This was previously not achievable, in particular because it was not possible to measure the lysis time exactly, as it was possible to measure coagulation time.

Embodiments for determining the activity of blood platelets by way of their ability to aggregate, in particular including embodiments in which blood platelet aggregation can be induced by substances such as adenosine diphosphate, collagen, thrombin, serotonin or epinephrin, ionophores, complement or streptolysin, are also encompassed by the novel method.

Other embodiments of the novel method can be used for determining the concentration, in particular in blood or plasma, or the efficiency of pharmaceuticals such as heparin, tPA, acetylsalicylic acid, coumarin derivatives, hirudin and streptase plasma factor concentrates, such as prothrombin complexes, factor VIII concentrate or vWF-containing factor concentrates, antibodies against platelet receptors such as GP IIb/IIIa complex, GP Ib/V/X complex, serotonin receptor, adenosin diphosphate receptor or thrombin receptor, contact phase inhibitors, such as bovine trypsin inhibitor or C1 esterase inhibitor, inhibitors of the coagulation system, such as inactivated factor VIIa, antibodies against tissue thromboplastin, tissue factor pathway inhibitor, antithrombin III, thrombomodulin or activated protein C, and also fibrin aggregation inhibitors.

They can also be used for the therapeutic drug-level monitoring of, for example, heparin, tPA, acetylsalicylic acid, coumarin derivatives, hirudin, contact phase inhibitors such as bovine trypsin inhibitor or C1 esterase inhibitor, or antibodies against platelet receptors or proteins which are associated on platelets, such as heparin/platelet factor 4 complex.

The invention also encompasses diagnostic agents which comprise one or more substances which, as a consequence of blood platelet aggregation, clot formation and/or clot dissolution are brought to a distance from each other which permits or prevents an interaction, in particular an energy transfer, between the substances and the extent of the interaction can be determined. This diagnostic agent can be employed for detecting an acquired or inherited hemostasis disturbance. In addition, the invention encompasses diagnostic agents which enable one or more of the different embodiments of the novel method to be implemented.

In that which follows, the invention is explained in more detail with the aid of examples and with reference to the enclosed figures.

The following abbreviations, inter alia, are used in the figures: "t"=measured time in seconds ("s"); measured signals: "A 405 nm"=absorption units in "mE" at 405 nm wavelength; "c"=counts as measured signal.

FIG. 1 shows the course of an APTT reaction for a normal plasma (NP) and a pathological plasma (PP) in a conventional turbidimetric method (FIG. 1a) and in the novel method (FIG. 1b). The ascertainment of the coagulation time by determining the point of intersection of the respective base line and the clot formation line is shown diagrammatically.

FIG. 3 shows the course of an APTT reaction for a normal plasma in a conventional turbidimetric method FIG. 3a) and in the novel method (FIG. 3b) when streptokinase is added for lysing the fibrin clot (A). For comparison, the course of the reaction without streptokinase is also given (B). The time of clot formation is in each case indicated by an arrow.

The following examples serve to clarify the novel method: the most important and basic hemostasis diagnostic tests were carried out using the example of particle-bound substances in accordance with the method of Ullman et al. (Clinical Chemistry (1996) 42: 1518–1526). While these methods are used in different versions as screening and also as single-factor tests, they are in the end always based on the same fundamental principle, namely that of determining the time which elapses until a measurable clot has formed or until this clot has dissolved once again.

Unless otherwise indicated, reagents from Dade Behring Marburg GmbH, Marburg, Germany, were used for the hemostasis tests.

EXAMPLE 1
Preparation of Sensitizer and Chemiluminescer Particles

The preparation of sensitizer and chemiluminescer particles is described in detail in EP 0 515 194, Clin. Chem. (1996) 42: 1518–1526 and Proc. Natl. Acad. Sci. (1994) 91: 5426–5430. The particles may have dextran coatings, for example, and additionally exhibit bound streptavidin (see also Proc. Natl. Acad. Sci. (1994) 91: 5426–5430). The preparation of one sensitizer and chemiluminescer particle variant is described below by way of example (see also EP 0 515 194, example 8, for further details):

Preparation of Sensitizer Particles:

A solution of chlorophyll a in benzyl alcohol (1.0 ml; 0.6 mM) is added to 8.0 ml of benzyl alcohol which has been heated to 105° C. A suspension of latex beads (175 nm, carboxyl-modified latex, Bangs Laboratories, Carmel, Ind.) in water (10%; 1.0 ml) is added to the benzyl alcohol solution. The mixture is stirred at 105° C. for 5 minutes and then cooled down to room temperature. 10 ml of ethanol are added and the mixture is centrifuged. The pellet is resuspended in a 1:1 water/ethanol mixture (10 ml) and then centrifuged once again. The same procedure is repeated with water and the pellet is then taken up in physiological sodium chloride solution.

Preparation of the Chemiluminescer Particles (=Acceptor Particles):

20 ml of the carboxyl-modified latex particle suspension (10% suspension in water) are mixed with 20 ml of 2-ethoxyethanol. The mixture is heated to 90° C. 20 ml of a solution of 10 mM dioxene, 20 mM europium chelate with the agent 3-(2-thienoyl)-1,1,1-trifluoroacetone (Kodak, CAS #14054-87-6) (EuTTA) and 60 mM trioctylphosphine oxide (TOPO) in 2-ethoxyethanol are added to the particle suspension. The mixture is heated for a further 7 minutes at 97° C. After it has been cooled down to room temperature, 40 ml of ethanol are added and the mixture is centrifuged. The pellet is then resuspended in 80% ethanol and centrifuged. This washing process is repeated with 10% ethanol. In conclusion, the particles are taken up in physiological sodium chloride solution.

EXAMPLE 2

Determination of the activated partial thromboplastin time (APTT) in a conventional method (turbidimetry) and in the novel method.

Conventional method: A pool of normal plasma (control plasma N; Prod. No. ORKE) and a pathological plasma (Pathoplasma II; Prod. No. OTXK) were measured in parallel in a conventional, optically measuring automated coagulation instrument (Behring Coagulation Timer; BCT) using pathromtin SL (Prod. No. OQGS). For this, 50 µl of sample were mixed with 50 µl of pathromtin SL and, after incubating at 37° C. for 2 minutes, coagulation was started by adding 50 µl of a 25 mM solution of calcium chloride (Prod. No. ORHO).

The activated partial thromboplastin time was determined in the novel method using pathromtin working solution, which was prepared from kaolin activator (Prod. No. OTXC) and phospholipid (Prod. No. OTXB) in accordance with the manufacturer's instructions, and a 25 mmol/l solution of calcium chloride (Prod. No. ORHO). The determination was carried out on a luminometer. The measuring unit is fitted with a 670 nm diode laser (30 mW light source) and a photon counting unit (Hamamatsu R 4632 photomultiplier tube). A filter combination comprising a short-pass filter and a long-pass filter, which combination permits light to be measured between 550 nm and 650 nm, was placed in front of the photomultiplier. The entire system was protected from surrounding light. A typical measurement procedure comprises a period of illumination with the light source and a subsequent second phase in which the photons emitted from the measured material are counted. This measurement procedure can be repeated as often as required depending on the desired time during which the measured material is to be observed. The illuminiation period is typically 0.1–3 sec. The measurement period can be within the same range. A phase without illumination or measurement can be intercalated between two measurement procedures, which phase can be selected depending on the number of necessary measurement points. In addition, substances bound to particles were used in accordance with the invention, i.e.:

chemiluminescer particles acceptor particles: 2.5 mg/ml in physiological sodium chloride solution;

sensitizer particles: 2.5 mg/ml in physiological sodium chloride solution.

The following samples were measured: 1 pool of normal plasma (control plasma P, Prod. No. OUPZ), 2 pathological plasmas which are prepared by absorbing the vitamin K-dependent coagulation enzymes (pathoplasma I, Prod. No. ORXK; pathoplasma II, Prod. No. OTXL), 1 pathological plasma which was prepared by diluting all the coagulation factors (control plasma P; Prod. No. OUPZ), and also a serum from a healthy blood donor.

The reagents were prewarmed to +37° C. before use. In order to implement the test, the components were mixed as follows:

200 µl of sample
100 µl of acceptor particles
25 µl of sensitizer particles
200 µl of pathromtin working solution The mixture was then incubated at +37° C. for 2 min and coagulation was started by adding 200 µl of 25 mM calcium chloride solution.

The signals were recorded over time.

Figure 1A:
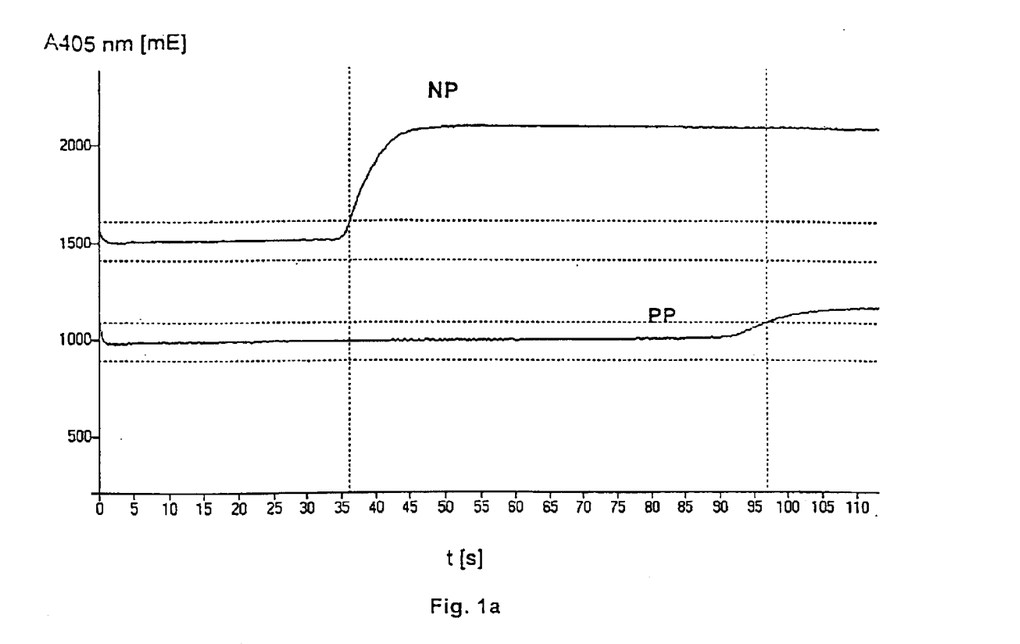
Figure 1B:
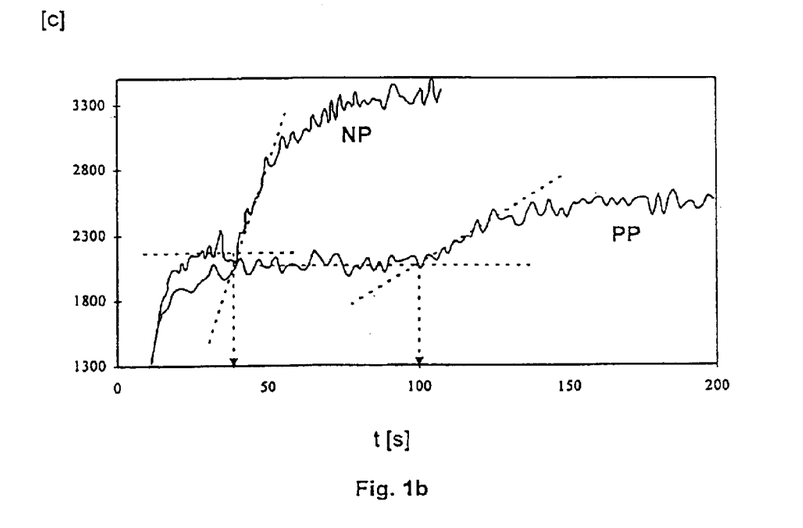

The coagulation times were ascertained from the curves which were obtained in the novel method by in each case carrying out a linear regression for the base line and the first 10 seconds of the reaction curve. The point at which these two lines intersected was taken to be the coagulation time (see also FIG. 1b).

Result: Table 1 shows that the plasma coagulation times which were determined in the novel method lie in the desired value range which was ascertained by the manufacturer using classical (mechanical and optical) methods. No signal was obtained with serum. While the coagulation enzymes of the respective branch of coagulation are active in serum, the fibrin clot has been removed. This demonstrates that, in the novel method, it is the formation of the clot, and not some particular effect of a coagulation enzyme on the added reagents, which is responsible for the production of the signal.

TABLE 1

APTT coagulation times which were obtained in the novel method (CECA), as compared with the desired values which were ascertained by the manufacturer using classical (mechanical and optical) methods, for various commercial plasmas. Values in sec.

| Sample | CECA | specified desired value range |
|---|---|---|
| Control Plasma N | 39.2 | 30.1–40.7 |
| Control Plasma P | 81.9 | 57.6–86.4 |
| Pathological plasma I | 67.1 | 51.2–76.8 |
| Pathological plasma II | 99.0 | 67–101 |
| Serum | no coagulation | |

EXAMPLE 3

Determination of the thromboplastin time (PT) in a conventional method (turbidimetry) and in the novel method.

The PT was determined using Thromborel S (Prod. No. OUHP), in accordance with the manufacturer's instructions, and the samples mentioned in example 2, with the determination taking place on an optically measuring coagulation instrument in the case of the classical optical method and on a luminometer in the case of the novel method.

On the BCT (turbidimetric measurement), 50 µl of pathological plasma I or pathological plasma II were in each case pipetted into a measuring chamber and the coagulation was started by adding 100 µl of Thromborel S.

On the luminometer, the components for carrying out the test were mixed as follows:

200 µl of sample

100 µl of acceptor particles

25 µl of sensitizer particles

The coagulation was started by adding

400 µl of Thromborel S.

The signals were recorded over time. The courses of the reaction kinetics were found to be practically identical, with an increase in turbidity being measured in the conventional method and an increase in chemiluminescence emission being measured in the novel method.

The courses taken by the reactions in the novel method were analysed as described in example 2. The results are listed in Table 2 in comparison with the coagulation times which are to be expected, according to information from the manufacturer, in conventional methods. Good agreement is found, just as in example 2. For the reason mentioned in example 2, there was no change in the measured signal when serum was used as the sample.

TABLE 2

PT coagulation times which were obtained in the novel method (CECA), as compared with the desired values which were ascertained by the manufacturer using classical (mechanical and optical) methods, for various commercial plasmas. Values in sec.

| Sample | CECA | specified desired value range |
|---|---|---|
| Control Plasma N | 14.7 | 9.5–14.3 |
| Control Plasma P | 30.7 | 18.8–28.2 |
| Pathological plasma I | 37.0 | 24.6–36.8 |
| Pathological plasma II | 56.0 | 40.7–61.1 |
| Serum | no coagulation | |

EXAMPLE 4

Determination of Coagulation in Whole Blood

It is not possible to determine a coagulation time in whole blood in conventional, optically measuring instruments since the optical density of the sample is too high. In the novel method, the reaction curve for a whole blood sample in an APTT was recorded as follows:

The reagents were prewarmed to +37° C. before use. For implementing the test, the components were mixed as follows:

100 µl of sample (citrate blood)

50 µl of acceptor particles 12.5 µl of sensitizer particles

100 µl of pathromtin working solution

The mixture was then incubated at +37° C. for 2 min and coagulation was started by adding 100 µl of 25 mM calcium chloride solution or of physiological sodium chloride solution.

These signals were recorded over time.

Figure 2:
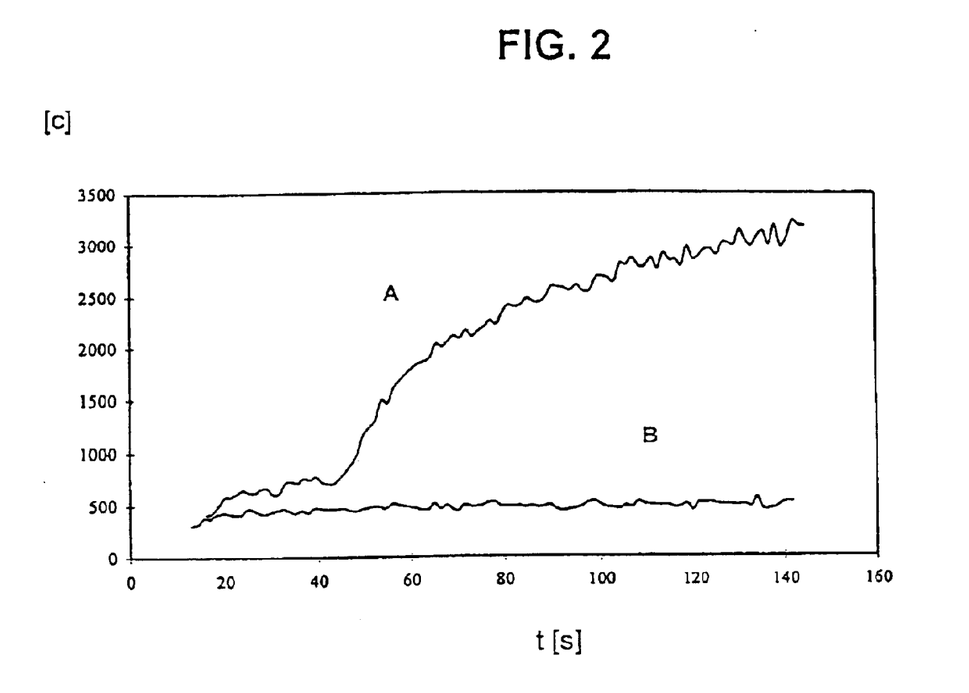
FIG. 2 shows the determination of the APTT of a whole blood sample in the novel method (A). For control, the test was carried out without adding calcium chloride (B).

The result is shown in FIG. 2. The reaction curve (B) which is obtained when no calcium chloride is added, and consequently no coagulation reaction is induced, is drawn in for comparison. The example shows that a reaction curve which is typical for coagulation, and which is produced due to the formation of a clot and is not, for example, induced by unspecific side reactions, is also obtained when whole blood is used as a sample.

Furthermore, due to its applicability to whole blood samples, the novel method proves to be more robust than conventional methods with regard to sample interference which is due to turbidity.

The fact that the novel method is less susceptible to interference from nonspecific turbidities which are present in the sample or in reagents already follows from example 2. In this example, an APTT in which kaolin (pathromtin) was used as the activator of the contact phase of the intrinsic coagulation system was carried out on a luminometer. Kaolin is a clay bank mineral in the form of silver lamellae. These lamellae generate such a high degree of light scattering that it is not possible to use this reagent in optically measuring instruments. For this reason, Pathromtin SL, which is another contact phase activator which was specially developed for optically measuring instruments, was used in the optically measuring instrument. Pathromtin SL comprises finely ground particles of silicon dioxide whose nonspecific light scattering is still tolerable.

EXAMPLE 5

Determination of Fibrinolysis Activity in the Novel Method.

Figure 3A:
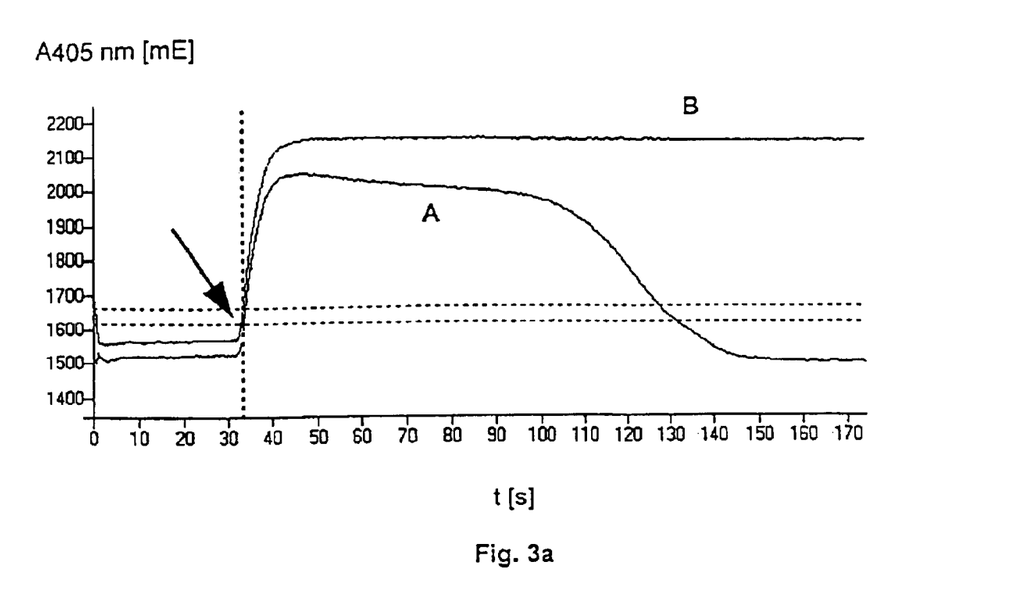

In order to determine fibrinolysis activity, a normal plasma (control plasma N, Prod. No. ORKE) and a whole blood sample were caused to coagulate in an APTT, using the novel method, as described in examples 2 and 4. At the same time as coagulation was induced, lysis of the clot which was forming was also induced by adding a streptokinase-containing solution (100 IU/ml of physiological sodium chloride solution; from Hoechst Marion Roussel). Streptokinase is a Streptococcus enzyme which enters into an active complex with plasminogen. This complex activates the plasminogen enzyme of the sample to form plasmin, which dissolves both fibrinogen and fibrin clots proteolytically. In conventional optical methods, this leads to the measured signal decaying continuously (see also FIG. 3a).

The reagents were prewarmed to +37° C. before use. For implementing the test, the components were mixed as follows:

100 µl of sample (control plasma N, ORKE)

50 µl of acceptor particles 12.5 µl of sensitizer particles

100 µl of pathromtin working solution

The mixture was then incubated at +37° C. for 2 min and coagulation was started by adding 7.2 µl of streptokinase solution (100 IU/ml of physiological sodium chloride solution)

100 µl of 25 mM calcium chloride solution.

Figure 3B:
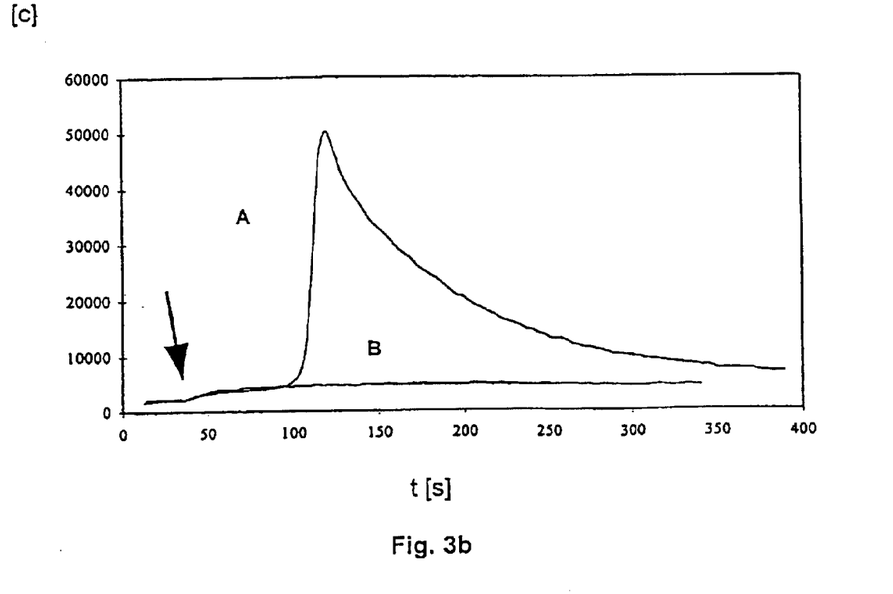

The signals were recorded over time (see FIG. 3b).

As a result of the incipient clot formation, the measured signal initially increases as in examples 2 to 4. The corresponding comparison curve without streptokinase is also drawn in in FIG. 3b and labelled "B". However, when streptokinase is present, there is an abrupt increase in the measured signal, which increase is more strongly pronounced in plasma than in a whole blood sample which was also measured, as lysis of the clot begins. This signal then decays slowly with time. This is an effect which has not previously been described. Since streptokinase is present ab initio and there is no change in the course of the reaction until clot formation begins, this abrupt increase in the signal cannot have been caused by side reactions in the streptokinase solution.

This example demonstrates an entirely novel diagnostic application of the novel method. The very powerful and rapid increase in the signal, which is due to dissolution of the clot and which also occurs in whole blood, enables the time of lysis to be determined very sensitively and in a novel manner. In previous methods (see also FIG. 3a), it was only the decrease in the signal, which also occurs in the present case, which was observed; however, this decrease in the signal takes place so slowly in conventional methods that it was not previously possible to measure the onset of lysis exactly. All of the documents cited in this application are incorporated by reference in their entirety.

We claim:

1. A diagnostic agent which comprises at least two primary substances which are not bound to a member of a specific binding pair, wherein as a consequence of blood platelet aggregation, clot formation and/or clot dissolution, the at least two primary substances can enter into interaction with each other when in spatial proximity, and wherein at least one of the at least two primary substances is able to bind nonspecifically to components of a blood clot.

2. A diagnostic agent as claimed in claim 1 for detecting an acquired or inherited hemostasis disturbance.

3. A diagnostic agent as claimed in claim 1, wherein the interaction directly or indirectly provides a signal.

4. A diagnostic agent as claimed in claim 1, wherein the interaction is an energy transfer.

5. A diagnostic agent as claimed in claim 1, wherein at least one of the at least two primary substances comprises all or part of a suspendable particle, or is associated with a suspendable particle.

6. A diagnostic agent as claimed in claim 1, wherein at least one of the at least two primary substances comprises a photosensitizer.

7. A diagnostic agent as claimed in claim 6, wherein the photosensitizer is selected from the group consisting of acetone, benzophenone, 9-thioxanthone, cosin, 9,10-dibromoanthracene, chlorophyll, buckminsterfullerene, methylene blue, Rose Bengal, porphyrins, phthalocyanines, and their derivatives.

8. A diagnostic agent as claimed in claim 1, wherein at least one of the at least two primary substances comprises a chemiluminescent compound.

9. A diagnostic agent as claimed in claim 8, wherein the chemiluminescent compound is selected from the group consisting of olefins, 9-alkylidenexanthans, 9-alkylidene-N-alkylacridans, enol ethers, enamines, arylvinyl ethers, dioxenes, aryl-imidazoles, and lucigenin.

10. A diagnostic agent as claimed in claim 1, wherein at least one of the at least two primary substances comprises a fluorescent compound.

11. A diagnostic agent as claimed in claim 10, wherein the fluorescent compound is subject to photooxidation, or react with singlet oxygen to give fluorophores.

12. A diagnostic agent as claimed in claim 11, wherein the fluorophores are selected from the group consisting of rhodamines, ethidium bromide, 5-dimethylamino-1-naphthalenesulfonyl, europium chelates, and ruthenium chelates.

13. A diagnostic agent as claimed in claim 10, wherein the fluorescent compound is selected from the group consisting of 1,3-diphenylisobenzofuran, umbelliferyl ethers, and umbelliferyl selenides.

* * * * *